US008414773B2

(12) United States Patent
Davison et al.

(10) Patent No.: US 8,414,773 B2
(45) Date of Patent: Apr. 9, 2013

(54) METHOD AND APPARATUS FOR CHROMATOGRAPHY USING SPHERICAL SILICA GEL

(75) Inventors: Dale A. Davison, Greenwood, NE (US); Ruth A. Pipes, Odell, NE (US); Jack E. Silver, Lincoln, NE (US)

(73) Assignee: Teledyne Instruments, Inc., Thousand Oaks, CA (US)

( * ) Notice: Subject to any disclaimer, the term of this patent is extended or adjusted under 35 U.S.C. 154(b) by 874 days.

(21) Appl. No.: 12/348,305

(22) Filed: Jan. 4, 2009

(65) Prior Publication Data
US 2009/0166294 A1    Jul. 2, 2009

Related U.S. Application Data

(63) Continuation-in-part of application No. 11/699,169, filed on Jan. 29, 2007, now abandoned.

(51) Int. Cl.
*B01D 15/08* (2006.01)
(52) U.S. Cl.
USPC .......................................................... 210/656
(58) Field of Classification Search ................. 73/61.56; 702/22, 23, 30, 31; 210/656, 635, 659, 739, 210/143, 198.2, 198.3
See application file for complete search history.

(56) References Cited

U.S. PATENT DOCUMENTS

| 3,418,084 | A | * | 12/1968 | Allington | ........................ | 422/70 |
| 6,267,942 | B1 | | 7/2001 | Mori et al. | | |
| 6,427,526 | B1 | * | 8/2002 | Davison et al. | ............... | 73/61.55 |
| 7,318,900 | B2 | * | 1/2008 | DeMarco | ....................... | 210/656 |
| 2005/0287062 | A1 | | 12/2005 | Aznar | | |
| 2006/0027490 | A1 | | 2/2006 | DeMarco | | |
| 2010/0252502 | A1 | * | 10/2010 | Witt | ............................... | 210/656 |

OTHER PUBLICATIONS

Example of RFID Tag used on Chromatography Column, for at least 4 years by Waters Corporation on Acquity UPLC Console (eCord) and Document Details, 2007.
Waters Corporation Press Release Jan. 11, 2007, referring to Acquity UPLC system introduced 2004.
Waters Corporation Press Release Feb. 28, 2005 regarding new column chemistries for Acquity UPLC.
Pages from Waters Corporation website for nanoAcquity UPLC System Overview, Enabling Technology and Related Solutions: UPLC and MS, 2007.
"Analysis of the enzymatic racemization of D-aspartic acid to L-aspartic acid by the on-line coupling of a solid-phase extraction column and a ligand-exchange high-performance liquid chromatography column" Cheanyeh Cheng, Shouh-Chwan Wu; Journal of Chromatography A, 896 (2000) 299-310.

* cited by examiner

*Primary Examiner* — Terry Cecil
(74) *Attorney, Agent, or Firm* — Suiter Swantz pc llo

(57) ABSTRACT

Sample is applied to a chromatographic column containing shape stabilized packing and the liquid phase is pumped through the shape stabilized packing at a rate of flow greater than the standard rate of flow to obtain at least one of a target resolution and target time of run. Because of the improved resolution provided by the shape stabilized packing at higher rates of flow of solvent, the chromatographer can either obtain better resolution with a standard gradient or shorten the time of the run and reduce the amount of solvent needed by increasing the slope of the gradient.

12 Claims, 7 Drawing Sheets

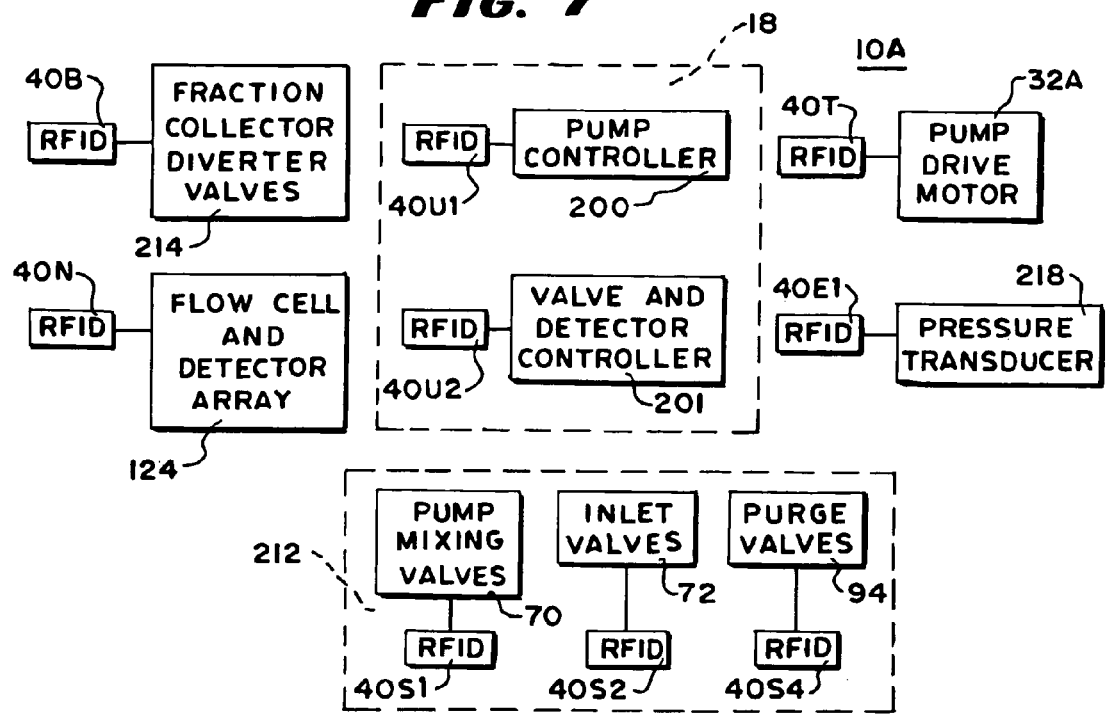
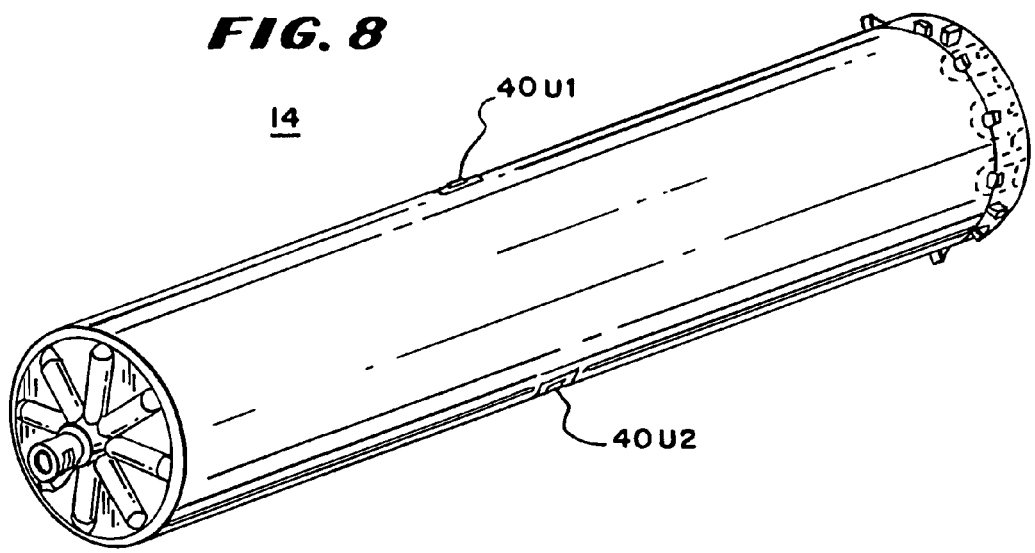

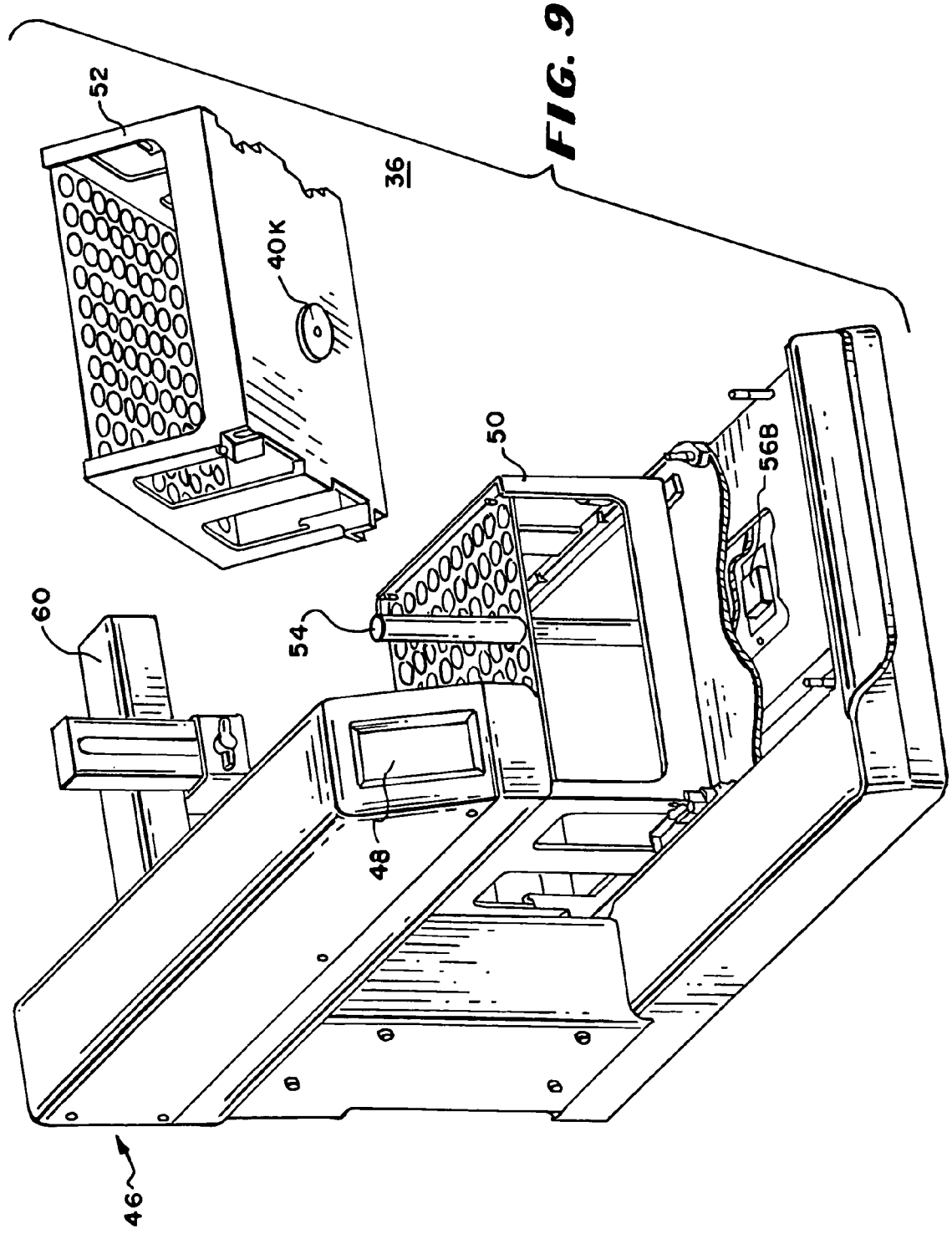

METHOD AND APPARATUS FOR CHROMATOGRAPHY USING SPHERICAL SILICA GEL

RELATED CASES

This application is a continuation-in-part of U.S. patent application Ser. No. 11/699,169 filed Jan. 29, 2007 now abandoned by Dale A. Davison, et al., entitled APPARATUSES AND METHODS FOR WIRELESS MONITORING AND CONTROL OF ENVIRONMENTAL SAMPLING AND CHROMATOGRAPHIC APPARATUSES.

BACKGROUND OF THE INVENTION

This invention relates to chromatography using spherical silica gel.

It is known to select the rate of flow in gradient based on the van Deemter equation or by using standard procedures which have their basis in the van Deemter equation. These conventional procedures work very well with silica particles of irregular shape.

It is also known to improve the resolution of liquid chromatography through the use of spherical packing material. For example, United States published application 2005/0287062 teaches having spherical and porous silica gel with granules comprised between 3 and 45 microns and pores comprised between 30 and 300 Angstrom units. Spherical silica packing was available at least by 1999, as shown by U.S. Pat. No. 6,267,942.

It has been the practice to select the optimum rate of flow of solvent and the gradient used in liquid chromatography based on the van Deemter equation or simply out of habit, originating with the values yielded in the past by the van Deemter equation. The van Deemter equation indicates that a plot of the plate height against rate of flow of the solvent is hyperbolic in shape so that the lowest point on the hyperbola approximates the optimal flow rate of the mobile phase for an efficient column.

Although these practices are long standing and uncontradicted in the field, they do not yield the best results.

SUMMARY OF THE INVENTION

Accordingly, it is an object of the invention to provide a novel method and apparatus for performing liquid chromatography.

It is a further object of the invention to provide a novel method and apparatus for improving the resolution of or decreasing the time for a chromatographic run.

It is a still further object of the invention to provide a novel liquid chromatographic system.

It is a still further object of the invention to provide a novel system and method for reducing the cost and/or time required for chromatography.

In accordance with the above and further objects of the invention, liquid chromatography is performed by applying sample to a column containing shape stabilized packing. For some applications, the mobile phase is pumped through the column at the standard rate of flow. Use of the standard rate of flow with the shape stabilized packing results in the target resolution being reached. In this specification, the words "standard rate of flow" means the rate of flow ordinarily used for separation of a sample in liquid chromatography with irregular packing. It is the rate of flow based on the optimum value or a slightly higher conventional value that are determined using the van Deemter equation. In this specification, the words "target resolution" mean desired amount of separation for the purpose of the chromatographic run. For example, for some separations such as preparatory separations, a very low resolution may be adequate whereas for some analytical separations and some preparatory separations, good resolution may be necessary.

In the alternative, the mobile phase may be pumped at the higher rate of flow herein referred to as an enhanced rate of flow. In this situation, a steeper gradient may be used to obtain both the target resolution and target time of run. In this specification, "enhanced rate of flow" means a rate of flow selected to make a significant increase in efficiency of the chromatographic separation. It is an increased flow rate of higher than the standard rate of flow for the sample. Generally, the enhanced rate of flow is at least 20 percent greater than the rate of flow that would normally be used as determined by the van Deemter equation or be determined by custom for use with irregular shaped silica gel and the same sample. Preferably, the enhanced rate of flow is approximately 50 percent greater than the standard rate of flow. The enhanced rate of flow permits a gradient shorter and steeper than a standard chromatography gradient for the sample with a column having spherical silica gel packing and at a rate of flow of solvent greater than used with a standard chromatographic run. In this specification, reference to "a steeper rate of flow" means that one of the solvents in the solvent mixture is increased in proportion to the total volumetric flow at a faster rate. Advantageously, the liquid chromatographic column has an inner diameter greater than 20 mm. The rate of flow and gradient are selected in accordance with the resolution required. To select the gradient, at least one pilot run is performed on the sample and the run time is shortened and the gradient and flow rate are increased for samples for which the at least one pilot run provides a resolution greater than needed. The pilot run may be thin layer or column chromatography.

A liquid chromatographic system comprises at least one column with spherical gel packing and a column mounting fixture adapted to receive the column. A detector is positioned to receive effluent from the column. The column has indicia that is detectable by the fixture when the column is connected to the fixture. In this specification, the word "indicia" means any arrangement that may communicate information about a column to the chromatographic system. The indicia may be a first wireless communication device. In this case, a second wireless communication device is arranged to receive a signal from the first wireless communication device and to communicate with the controller. However, any type of indicia may be used including a physical switch that is activated by pressure from a column, reed relays that are activated by a magnet on the column, optical readouts such as used with bar codes or any other type of detectable indicia. The controller has a program containing instructions controlling the rate of flow of solvent in the at least one column. The first wireless communication device includes an indication of whether the packing is a spherical gel packing. A display indicates to an operator that the column includes a spherical gel packing wherein the operator may select a higher flow rate setting than the standard flow rate setting. The controller communicates wirelessly with the first wireless communication device and the second wireless communication device communicates wirelessly through a third wireless communication device.

For some preparatory or quality control operations, data representing a chromatographic curve for a chromatographic column is recorded in a first wireless communication device attached to the chromatographic column. This curve is read when the chromatographic column is inserted into a column mounting fixture on a liquid chromatographic system. The data representing a chromatogram is received on a second wireless communication device communicating with a controller for the liquid chromatographic system. The controller controls the pumping system to pump the solvents to the chromatographic column in accordance with the sequence of solvent conditions transmitted to the controller to perform the known separation on the sample."

The data representing a chromatographic curve for a chromatographic column is recorded in a first wireless communication device for the selected separation attached to the chromatographic column. When the chromatographic column is inserted into a column mounting fixture on a liquid chromatographic system, the controller receives data representing a chromatogram on a second wireless communication device communicating with the controller for the liquid chromatographic system.

The data representing the sequence of solvent conditions for the chromatographic curve is transmitted from the second wireless communication device to a third wireless communication device communicating with a pumping system within the liquid chromatographic system. Solvents are pumped in accordance with the sequence of solvent conditions transmitted to the third wireless communication device to pump the solvent to the chromatographic column.

In one embodiment, at least one gradient run is programmed with at least one gradient profile for a sample. The gradient profile uses a rate of flow of solvent higher than the standard rate of flow. The chromatographer determines whether the gradient profile provides a target resolution and a target time of run resolution for the sample. In this specification, the words "target time of run" mean the desired time for a chromatographic run. For example, in some situations, it may be the shortest time for the run obtainable with the target resolution which is low. This is a possible target time of run for preparatory chromatography.

TLC may be used to determine whether the target resolution and target time of run are met or pilot runs may be used to determine whether the target resolution and target time of run are met. In adjusting the rate of flow when the target resolution is not met, a pilot run is made increasing the rate of flow of solvent by at least 10 percent and the gradient slope by at least 10 percent for a first trial run and decreasing the rate of flow of solvent and decreasing the gradient for pilot runs in which the target resolution is not met and increasing the rate of flow and the gradient for pilot runs in which the target resolution is exceeded. Preferably, however, the rate of flow is increased by 50 percent.

More specifically, to identify, separate or purify a target component using column chromatography, the resolution with a standard gradient is determined. In this specification, the words "target component" mean a component of a sample or mixture that is the subject of liquid chromatography. It is one of the materials of interest and is sometimes referred to as the material of interest or target compound. It is the component that is to be identified, separated or purified. When considering any two TLC spots rather than the spots caused by a target component and the closest impurity, the primary component is the component of the mixture that has a retention factor closest to the preferred retention factor at a bracketing solvent strength.

For identifying a poorly resolved target compound with a high equivalent plate height, a chromatographic run is made with a gradient no greater than the standard but with a flow rate greater than the standard flow rate and for separating or purifying a well resolved target component, a chromatographic run is made at a higher flow rate and a gradient slope steeper than the standard gradient. In this specification, the words "gradient slope" means the rate at which the proportion of one liquid to the total mixture of liquids changes.

To make an inexpensive flash chromatographic column, a tubular body is molded from plastic, filled with spherical or spheroid-like granules and closed. Preferably, before closing, at least one column adjusted retaining plate is pressed into the tubular body to hold frits in place. The frits compress the spherical or spheroid-like granules. The packing, frits and retaining plates are selected to increase the pressure rating of the flash chromatographic column and thus permit a wider range of materials to be separated by flash chromatography. Pressure is applied to the column adjusted retaining plate during the assembly of the column sufficient to form a design-pressure packing.

In performing flash chromatography, solvent is caused to flow from at least one source of solvent through an inlet port of a column. The solvent flows toward an interior of the column, causing the solvent to flow through frit, through spherical or spheroid-like derivitized packing material in its path between an inlet port and an outlet port and through at least one column adjusted retaining plate. The column is disposed of after between one and ten chromatographic runs and a new column is connected.

More broadly, a multiple fraction instrument is provided that includes at least one pumping system, at least one flow path, a flow path mounting fixture, a container mounting fixture adapted for receiving at least one container and a controller. The at least one pumping system has a first wireless communication device and the controller has a second wireless communication device. There is at least one other component of the multiple fraction instrument that has a third wireless communication device. The second wireless communication device is positioned to communicate wirelessly with at least the first and third wireless communication devices.

In this specification, the words, "multiple fraction instrument or process" means instruments or processes used in scientific or investigative work such as in the separation sciences or environmental studies that process multiple fractions or samples or component parts in a manner that requires identification or control of individual fractions or component parts or samples or the recall of information about individual ones of the fractions or component parts or samples. The words "wireless communication device" means a device that can either receive and/or transmit information wirelessly and may or may not have a non-volatile memory for storing information such as data or programs that can be transmitted, altered or sequenced or received. A wireless communication device may be either a transmitter or a reader or a transceiver or any combination of these. In the preferred embodiment, they are RFID devices but may be Bluetooth or Wi-Fi or Zigbee or any other wireless system.

In the operation of the liquid chromatograph, data representing a chromatographic curve for a chromatographic column is recorded in a first wireless communication device attached to the chromatographic column. This curve is read when the chromatographic column is inserted into a column mounting fixture on a liquid chromatographic system. The data representing a chromatogram is received on a second wireless communication device communicating with a controller for the liquid chromatographic system. Data representing the sequence of solvent conditions for the chromatographic curve is transmitted from the second wireless communication device to a third wireless communication device communicating with a pumping system within the liquid chromatographic system. The data is used to pump the solvents to the chromatographic column in accordance with the sequence of solvent conditions transmitted to the third wireless communication device.

In some embodiments, data is wirelessly transmitted to the second wireless communication device from a fourth wireless communication device communicating with at least one detector positioned to receive effluent from the chromatographic column and data is transmitted from the second wireless communication device to a readout device to indicate peaks detected by the detector and to a fraction collector to activate collection of bands. In another embodiment, there is a controller having a gradient program stored within it and a first wireless communication device electrically connected to and communicating with the controller to transmit information to a pumping system. The pumping system in a preferred embodiment includes at least two syringe pumps and at least two sources of liquid although other types of pumps such as reciprocating pumps and the like may be used. The pumps may include at least one wireless communication device which receives data from a wireless communication device on the controller to control pumping rates. In the alternative, the chromatographic system may include at least one time proportioning electronically controllable liquid gradient switching valve and a second wireless communication device communicating with the at least one time proportioning electronically controllable liquid gradient switching valve.

The switching valve is connected to switch liquid flow from one or the other of the at least two sources of liquid to an inlet of at least one of the at least two syringe pumps. The first and second wireless communication devices are wired to transmit switching times of the at least one time proportioning electronically controllable liquid gradient switching valve to form gradient stored in the controller. One of the at least two syringe pumps is used for each one of multiple channels. Each of the at least two syringe pumps has a displacement of at least five milliliters and one of the at least two syringe pumps has a discharge outlet connected to a sample injection device and thence to a chromatographic column. The wireless communication device includes a memory. The memory has data recorded in it representing a starting concentration of a solvent whereby the chromatographic system may separate a preselected component of a sample with the starting concentration of the solvent. The memory has data recorded in it representing a chromatographic curve with a starting concentration for purifying the preselected component of a sample and an ending point.

A chromatographic column includes an inlet end having an inlet port, an outlet end having an outlet port, tubular side walls between the inlet end and the outlet end, at least one wireless communication device on at least one or more of the inlet end, outlet end or tubular side walls. The at least one wireless communication device may include a nonvolatile memory having data recorded on it and the data may include a precision of the column from run to run, data indicating a make and model of the column, a date of manufacture and a lot number of the column.

From the above description, it can be understood that the methods and apparatuses of this invention have several advantages, such as: (1) the time required for identifying, separating or purifying sample can be reduced; (2) the amount of solvent is reduced; and (3) an instrument for reducing the time for separating, purifying or identifying material is easy to operate.

BRIEF DESCRIPTION OF THE DRAWINGS

The above noted and other features of the invention will be better understood from the detailed description when considered in connection with the following drawings, in which:

FIG. 7 is a block diagram of a chromatographic system in accordance with an embodiment of the invention;

FIG. 8 is a simplified perspective view of a column having a wireless communication device communicating with it;

FIG. 9 is a perspective view of a fraction collector in accordance with an embodiment of the invention.

DETAILED DESCRIPTION

Figure 1:
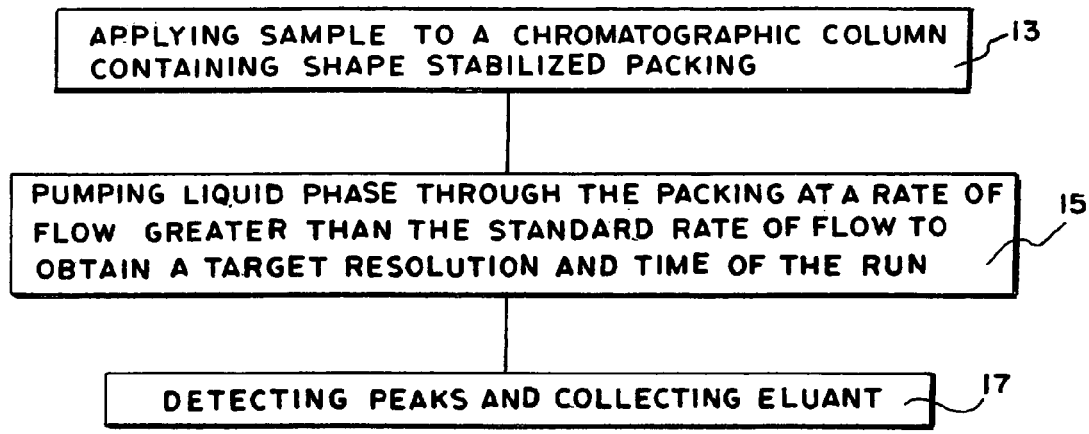
FIG. 1 is a flow diagram of a process for performing liquid chromatography using shape stabilized packing in a chromatographic system in accordance with an embodiment of the invention.

In FIG. 1 there is shown a flow diagram 11 of a process of performing liquid chromatography using a column having shape stabilized packing comprising a step 13 of applying a sample to a chromatographic column containing shaped stabilized packing, a step 15 of pumping liquid phase through the packing at a rate of flow greater than the standard rate of flow to obtain a target resolution and target time of the run, and a step 17 of detecting peaks and collecting eluant. In this specification, the words "shape stabilized" means particles, granules or packing material without shaped edges or thin portions that can be easily separated from the main body of the particle or granule of a shape that resists breaking to create fines. They are generally formed only of curved surfaces such as spheres or spheroid-like particles, granules or packing.

It has been discovered that the standard rate of flow as determined by the van Deemter equation or as used conventionally with values determined in the past such as by the van Deemter equation does not produce optimum results. Instead, increasing the rate of flow above the standard results in markedly improved resolution and efficiency. Thus, instead of attempting to maximize resolution by adjusting the gradient alone or attempting to shorten the time of the chromatographic run and reduce the amount of solvent by altering the gradient, it has been found more effective to increase the rate of flow of solvent prior to either maximizing the resolution or shortening the time of the gradient run.

Figure 2:
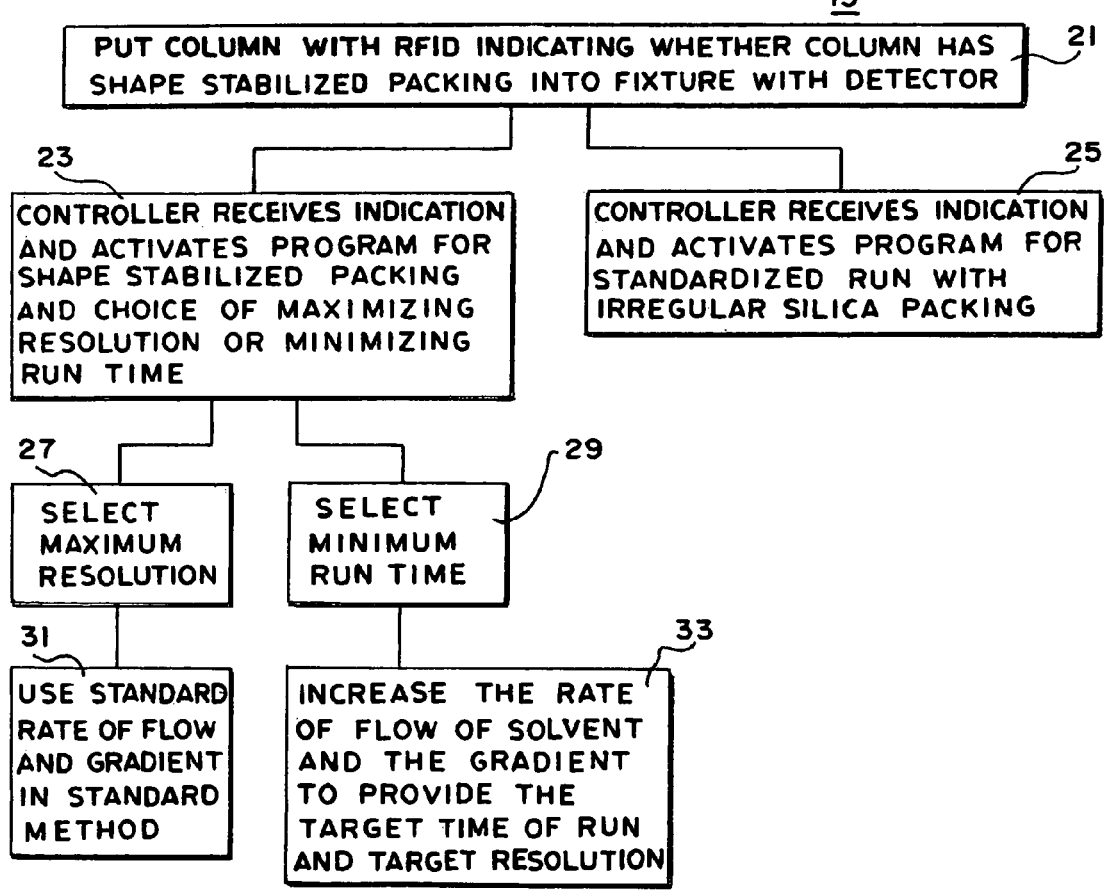
FIG. 2 is a flow diagram of a process for simplifying the performing liquid chromatography system in accordance with another embodiment of the invention.

In FIG. 2, there is shown a flow diagram 19 of a process for simplifying chromatography comprising the step 21 in which a signal is automatically generated when a column containing shaped stabilized packing is inserted into the chromatographic system and the controller receives an insertion indication for a column with shaped stabilized packing, the step 23 in which the controller causes the display of a selection program for maximum resolution or minimum time for the chromatographic run, the step 25 of activating the program for a standardized run with irregular silica packing, the step 27 of selecting the maximum resolution or the step 29 of selecting the minimum time for the run. If the step 27 for selecting the maximum resolution is taken, the standard rate of flow of solvent and the standard gradient slope is used. If the step 29 for selecting the minimum time for the run is selected, the rate of flow of solvent is increased as shown in step 33 and the gradient adjusted until the target time for the gradient run is reached.

Figure 3:
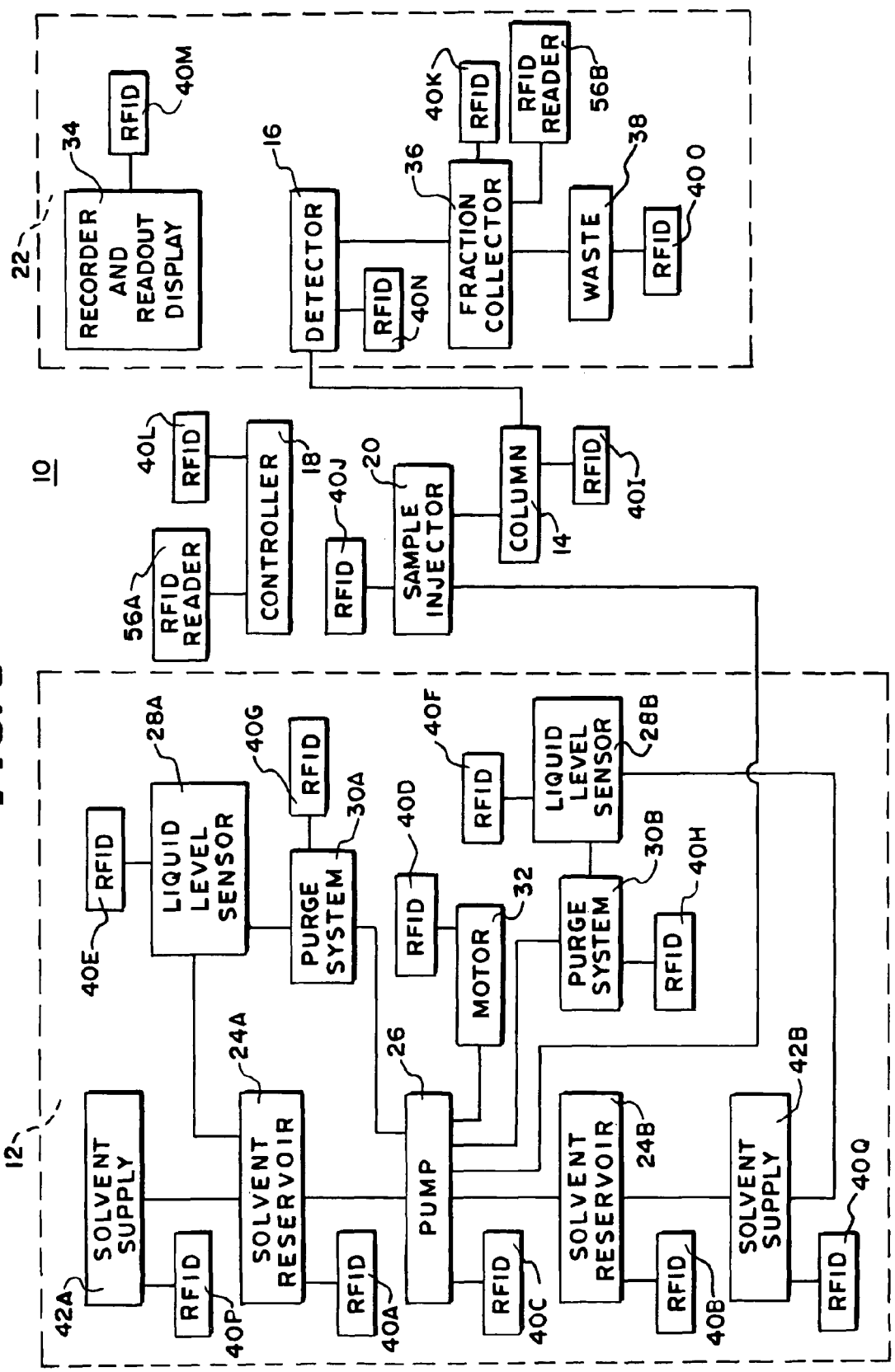
FIG. 3 is a block diagram of a liquid chromatographic system in accordance with an embodiment of the invention.

In FIG. 3, there is shown a block diagram of one embodiment of liquid chromatographic system 10 that may use the method and apparatus of this invention having a pumping system 12, a controller 18, at least one chromatographic column 14, a sample injector 20, a detector 16, and an analysis and collection system 22. In the preferred embodiment, an array of columns, detectors, sample collectors, pumps and pump motors would be utilized as described more completely in U.S. Pat. No. 6,427,526 granted Aug. 6, 2002, to Davison, et al., but the invention is equally applicable to any chromatographic system including the single column system shown in FIG. 3 and any other multiple fraction instrument such as environmental waste water collection systems. In this specification, "multiple fraction instruments" shall mean instruments used in scientific or investigative work such as in the separation sciences or environmental studies that process multiple fractions or samples or component parts in a manner that benefits from identification or control of the individual fractions, samples or component parts or the recall of information about individual ones of the fractions or samples or component parts.

The pumping system 12 in the embodiment of FIG. 3 includes first and second solvent reservoirs 24A and 24B, at least one pump 26 driven by at least one pump motor 32, liquid level sensors 28A and 28B communicating with the solvent reservoirs 24A and 24B respectively and purge systems 30A and 30B. The pumping system 12 supplies solvent to the column 14 and detector 16 or in the case of a preparatory liquid chromatographic system utilizing an array of columns and detectors, to the arrays of columns and detectors. The supply of solvent is under the control of the controller 18. The purge systems 30A and 30B communicate with the pump or pumps 26 to purge the pumps and the lines between the pumps and the column between chromatographic runs. The pump or pumps 26 supply solvent to the column or columns 14 or to the detector or detectors 16 under the control of the controller 18.

The controller 18 receives signals from the detector or detectors 16 indicating bands of solute and activates a fraction collector 36 and readout display 34 in a manner known in the art. One suitable fraction collection system is the FOXY® 2 fraction collector available from Teledyne Isco, Inc., 4700 Superior Street, Lincoln, Nebr. 68504.

To supply solvent to the pump or plurality of pumps 26, the pumping system 12 includes a plurality of solvent reservoirs such as the reservoirs 24A and 24B. In the case in which a plurality of pumps are utilized, the solvent reservoirs 24A and 24B will communicate with the pumps 26 through a manifold that channels solvent to each of the pumps 26. Each of the pumps 26 may also include a separate motor or one motor may drive pistons from the plurality of pumps 26 such as the motor or plurality of motors 32. In some embodiments, there is a purge system such as the purge systems 30A and 30B for purging the pump or pumps 26 and the connecting conduits. In the preferred embodiment, the solvent reservoirs 24A and 24B communicate with corresponding liquid level sensors 28A and 28B that sense the amount of solvent in the reservoirs 24A and 24B so that the reservoirs may continue to have solvent while the system is operating.

The column or columns 14 and detector or detectors 16 receive the solvent from the pumping system 12 in a manner known in the art. The sample injector 20 injects sample into the column 14 so that the solvent system may separate the components of the sample and carry them through the detector or detectors 16 and to the analysis and collection system 22. In an embodiment of the invention, the column 14 includes shape standardized packing. In this embodiment, an RFID device 40I has three fields. One of the fields indicates the size of the column, another contains information about the material packed in the column and the third field indicates that the column contains shape standardized packing. If a column, is inserted into the system that does not contain the shape standardized packing or if the chromatographic system 10 is not programmed to support columns with size standardized columns, the controller 18 is caused to use a program that is maximized for irregular silica and thus uses standard flow rates. The controller may be communicated with through either the RFID 40I or the RFID 40D or by hard wiring The analysis and collection system 22 includes the fraction collector 36, the detector 16 and the recording and readout display 34. The fraction collector 36 collects solute from the column or columns 14 and permits unselected material to flow through a waste system 38. The detector 16 also receives the solute and applies signals to the controller 18, which in turn controls the fraction collector 36 and the readout display 34 to provide signals indicating the separate species to be collected by the fraction collector 36 and to provide a read out to the user.

At least some of the solvent reservoirs 24A and 24B, purge systems 30A and 30B, liquid level sensors 28A and 28B, pumps 26, pump motors 32, controllers 18, sample injectors 20, columns 14, detectors 16, readout display or displays 34 and fraction collectors 36 include one or more RFID devices. While in FIG. 3, the liquid chromatographic system has these components hardwired together, each of these components may communicate through a separate one of RFID devices 40A-40Q.

In operating the chromatographic system 10 or similar chromatographic systems using wireless transmitters as a substitute for hardwiring between at least some of the components, the controller 18 supplies packets of data to the RFID 40L and the RFID 40L transmits the data to other units or receives data and transmits it to the controller 18. For example, in a gradient run, the solvent reservoir 24A is connected to the RFID 40A and the solvent reservoir 24B is connected to the RFID 40B. With this arrangement, the RFID 40A identifies the solvent within the solvent reservoir 24A and the RFID 40B identifies the solvent within the solvent reservoir 24B.

During the chromatographic run, the controller 18 supplies gradient information to the RFID 40L which transmits to the RFID 40D to operate the motor or motors 32. They in turn operate the pumps 26 to pump solvent from the solvent reservoirs 24A and 24B. The RFID 40C for the pumps 26 may provide feedback information by delivering packets of information concerning the pumping from their respective reservoirs to the RFIDs 40A and 40B, which in turn transmits the information to the controller 18 to which it is connected. In this way, the controller 18 through packets of data may control the gradient as it is pumped through the column 14. At the beginning of a gradient run, the controller 18 may transmit data to the RFID 40L which in turn may transmit data to the RFID 40J to initiate the injection of a sample from the sample injector 20 into the column 14. In the case of preparatory chromatography, the column 14 may contain in the RFID device 40I that cooperates with it a chromatogram to supply information to the controller 18 by transmitting packets of information from the RFID 40I connected to the column 14 to the RFID 40L connected to the controller 18. This information may enable the controller 18 to transmit information from its RFID 40L to the RFID 40D for the pump motors 32 and the pump or pumps 26 through their respective RFID to pump the desired solvent concentration for the preparatory purification. If the solvent runs low in one of the solvent reservoirs 24A or 24B, the liquid level sensors 28A and 28B supply this information to their respective RFID devices 40E and 40F which may transmit information to the appropriate one of solvent supplies 42A and 42B to replenish the supply of the solvent in the solvent reservoirs 24A and 24B.

During the chromatographic run, the controller 18 receives information from the detector 16. This information may be transmitted by the RFID 40N connected to the detector 16 to the RFID 40L connected to the controller 18. The controller 18 may in turn transmit this information to the read out display 34 by supplying the information to its RFID 40L which may transmit it wirelessly to the RFID 40M which in turn may supply it to the read out display 34. Similarly, the detector 16 may transmit information from its RFID 40N to the RFID 40K connected to the fraction collector 36 to activate the fraction collector 36 to collect peaks detected by the detector 16. Moreover, the RFID 40N connected to the detector 16 may supply this information to the controller 18 through its RFID 40L. The controller 18 may in turn supply information through its RFID 40L to the RFID 40K on the fraction collector 36 to control the positioning of collecting containers with respect to the inlet to the fraction collector 36 to supply bands to predetermined containers and follow a pattern that may be stored in the controller 18 if desired. A RFID reader 56B may read RFIDs on racks or other collector container holders and provide signals to the controller 18 indicating proper registration of the proper rack or information about which location in a rack is to receive a fraction.

While in the preferred embodiment, the individual components of the liquid chromatographic system 10 such as the detector 16, pumps 26, solvent reservoirs 24A and 24B and the like communicate directly with the controller 18 which may in return send signals to other units such as the readout display 34, other communication paths may be used. In the preferred embodiment, the center of communication is the wireless communication device 40L that communicates with the controller 18, which has substantial memory in it. Therefore, it is possible, for example, for the detector 16 to communicate directly with the readout display 34 to display peaks rather than transmitting the peaks to the controller 18 through the wireless communication device 40L and having the wireless communication device 40L transmit the peaks to the readout display 34 and fraction collector 36 through their respective wireless communication devices 40M and 40K. However, hard wiring may be used as a substitute for any or all of the wireless communication paths described above.

Figure 4:
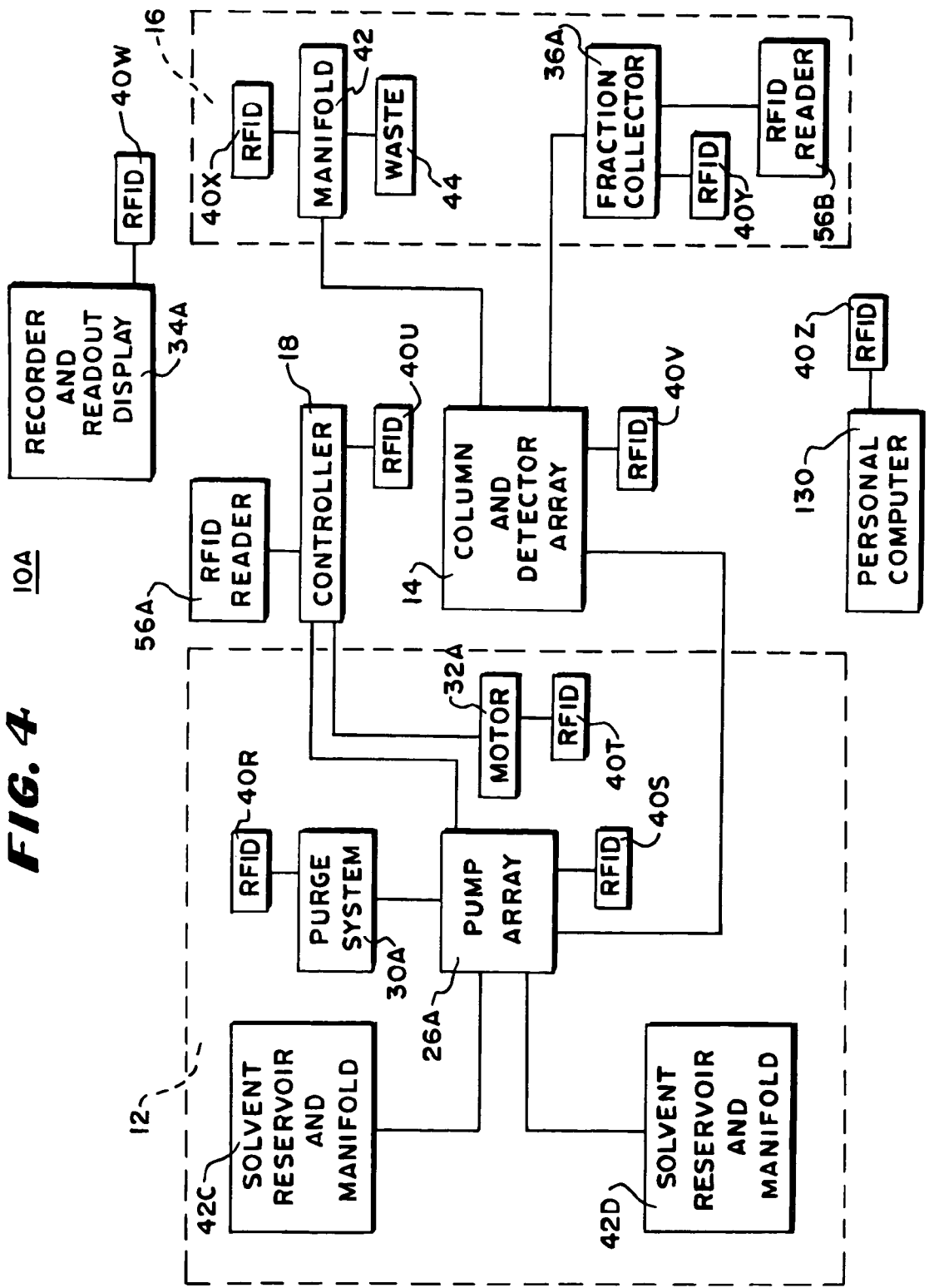
FIG. 4 is a block diagram of a preparatory liquid chromatographic system in accordance with another embodiment of the invention.

In FIG. 4, there is shown a block diagram of a preparatory liquid chromatographic system 10A having a pumping system 12, a column and detector array 14, a collector system 16, a controller 18, a purge system 30A and a personal computer 130. The personal computer 130 communicates with a wireless communication device 40Z. The pumping system 12 applies solvent to the column and detector array 14 under the control of the controller 18. The controller 18 supplies signals to a motor 32A which drives a pump array 26A by wirelessly transmitting signals from the RFID 40U electrically connected for communication with the controller 18 to the RFID 40T electrically connected for communication with the motor 32A. The movement of the pump array 26A provides a signal to the RFID 40S connected to it which transmits the signals in return to the RFID 40U so that a jam or interruption is sensed and the controller 18 receives a feedback signal indicating proper movement of the pump array 26A to pump liquid from solvent reservoir and manifolds 42C and 42D to the column and detector array 14 from which a fluid flows into the collector system 16 under the control of the controller 18.

Signals from the detectors in the column and detector array 14 are transmitted by the RFID 40V to the RFID 40U that communicates with the controller 18. The controller 18 in turn sends signals reflecting the detection of bands to a readout display 34A by transmitting them wirelessly to the wireless communication device 40W that communicates with the readout display 34A. Signals transmitted by the wireless communication device 40U from the controller 18 are also received by the wireless communication device 40Y that communicates with a fraction collector 36A to collect samples in a manner known in the art. A suitable fraction collector system is the FOXY® 200 fraction collector available from Teledyne Isco, Inc., 4700 Superior Street, Lincoln, Nebr. 68504. The chromatographic system shown in FIG. 4 and described herein is also described without the wireless system in U.S. Pat. No. 6,427,526 the disclosure of which is incorporated herein by reference.

To supply solvent to the pump array 26A, the pumping system 12 includes a plurality of solvent reservoirs and manifolds, a first and second of which are indicated at 42C and 42D respectively, the pump array 26A and the motor 32A which is driven under the control of the controller 18 to operate the array of pumps 26A in a manner to be described hereinafter. The controller 18 also controls valves in the pump array 26A through the wireless communication device 40S to control the flow of solvent and the formation of gradients as the motor 32A actuates pistons of reciprocating pumps in the pump array 26A simultaneously to pump solvent from a plurality of pumps in the pump array 26A and to draw solvent from the solvent reservoirs and manifolds such as 42C and 42D.

While in the preferred embodiment, an array of reciprocating piston pumps are used, any type of pump is suitable whether reciprocating or not and whether piston or not. A large number of different pumps and pumping principles are known in the art and to persons of ordinary skill in the art and any such known pump or pumping principles may be adaptable to the invention disclosed herein with routine engineering, and in most cases, one motor drives a plurality of pumps. While two solvents are disclosed in the embodiment of FIG. 4, only one solvent may be used or more than two solvents may be used. Because of the operation of a plurality of pumps simultaneously driven by a single motor, efficiency and cost reduction are obtained by this pumping mechanism.

To process effluent, the collector system 16 includes the fraction collector 36A to collect solute, a manifold 42 and a waste depository 44 to handle waste from the manifold 42. One or more fraction collectors 36A communicate with the column and detector array 14 to receive the solute from the columns either with a manifold or not. The manifold 42 may be used to combine solute from more than one column and deposit them together in a single receptacle or each column may deposit solute in its own receptacle or some of the columns each may deposit solute in its own corresponding receptacle and others may combine solute in the same receptacles. The manifold 42 communicates with the column and detector array 14 to channel effluent from each column and deposit it into the waste depository 44. The fraction collector 36A may be any suitable fraction collector such as that disclosed in U.S. Pat. No. 3,418,084 or the above-identified FOXY® fraction collector.

The wireless communication device 40U attached to the controller 18 in the preferred embodiment transmits information to the wireless communication device 40Z which records the information in an electronic notebook stored in the memory of the personal computer 130 in a manner known in the art. There are many electronic notebook systems and they have formatting as part of the program. For example, Waters Laboratory Informatics notebook will log all operations performed and prepare customized reports.

Figure 5:
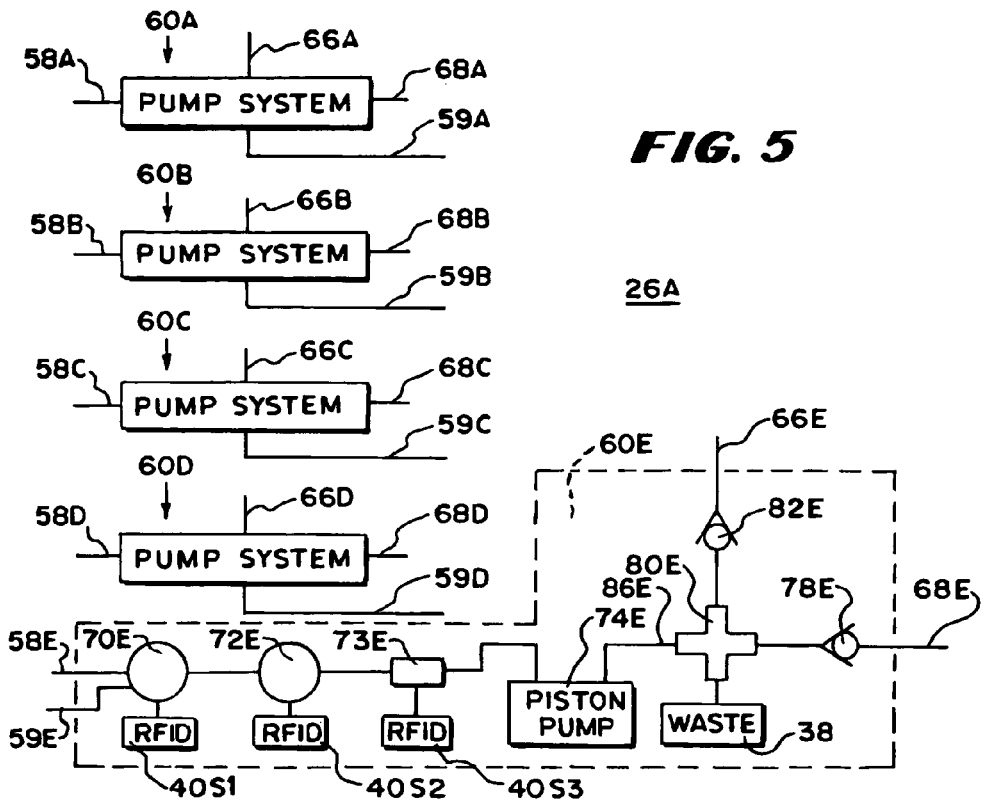
FIG. 5 is a schematic block diagram of a pump array in accordance with an embodiment of the invention.

In FIG. 5, there is shown a schematic block diagram of a pump array 26A having a plurality of piston pump systems 60A-60J (piston pump systems 60A-60E being shown for illustration in FIG. 5) although in the preferred embodiment there are ten such pumps each arranged to communicate with corresponding ones of ten outlets from the manifolds of the solvent reservoir and manifolds 42C and 42D (FIG. 4) to pump solvent from the reservoirs and manifolds 42C and 42D into corresponding ones of the columns (not shown in FIG. 5). In FIG. 5, four of the pump systems 60A-60D are shown in block form and a fifth pump system 60E is shown in greater detail with the understanding that each of the ten pump systems are substantially identical so that the explanation of the pump system 60E is an adequate explanation of all of the pump systems.

Each of the pump systems communicates with a corresponding one of manifold outlets 58A-58J (58A-58E being shown in FIG. 5) and 59A-59J (59A-59E being shown in FIG. 5) to receive two different solvents for the purpose of forming a gradient. They may also communicate with a source of purge fluid as indicated by purge conduits 66A-66J (66A-66E being shown in FIG. 5). With this arrangement, each of the pumps draws solvent into it from the solvent reservoirs in the solvent reservoirs and manifolds 42C and 42D (FIG. 4). The solvent flows from the pumps through a corresponding one of outlets 68A-68J (68A-68E being shown in FIG. 5).

The pump system 60E includes an inlet conduit or manifold outlet 58E from the first solvent reservoir and manifold 42C (FIG. 4), an inlet conduit or manifold outlet 59E from the second solvent reservoir and manifold 42D (FIG. 4), a three-way solenoid valve 70E, a two-way solenoid valve 72E, and a long flow conduit 73E, a reciprocating piston pump 74E and a check valve 78E. With this arrangement, the two different solvents from the conduits 58E and 59E are applied to the pump 74E through a common point connecting the three-way solvent valve 70E and the two-way solvent valve 72E. In the preferred embodiment, two cycles of solvent are applied for each stroke of the piston pump 74E. The size of the cylinder, the size of the flow conduit 73E, the speed of the refill and delivery strokes of the piston are selected to ensure mixing within the pump 74E and flow conduit 73E to pump a formed gradient through a conduit 80E, through the check valve 78E and an outlet conduit 68E to the column and collector array 14 (FIG. 4). For this purpose, the pump cylinders are in the range of one inch to eight inches long. In the preferred embodiment, the cylinders are 3.5 inches long.

To provide two injections or charges of solvent during a refill portion of a pump cycle, the two-way electronically controlled solvent valve 72E opens once during each piston refill stroke of the pump 74E under the control of a signal received from wireless communication device 40S2 which receives a signal wirelessly from the wireless communication device 40U (FIG. 4) that communicates with the controller 18 (FIG. 4). Enclosures join the delivery portion of the pump cycle. In the preferred embodiment, the two-way valve 72E is a solenoid valve. To provide a gradient, the three-way electronically-control proportioning valve 70E switches between the two solvent reservoirs several times during each refill stroke in response to a signal from the wireless communication device 40S1 in communication with it. The wireless communication device 40S1 receives a signal for this purpose from the controller 18 (FIG. 4) by wireless transmission from the wireless communication device 40U (FIG. 4) to open to the first solvent reservoir and manifold 42C (FIG. 4) and then to the second solvent reservoir and manifold 42D (FIG. 4) to provide both solvents in two stages for better mixing. The proportion of the time the three-way valve 70E is open to the first solvent reservoir and manifold 42C (FIG. 4) and then to the second solvent reservoir and manifold 42D (FIG. 4) determines the composition of the mixture in the gradient. Both of the solenoid operated valves 70E and 72E are under the control of the controller 18 (FIG. 4) to which they electronically communicate through wireless communication devices 40S1, 40S2 and 40U (FIGS. 3 and 4).

Figure 6:
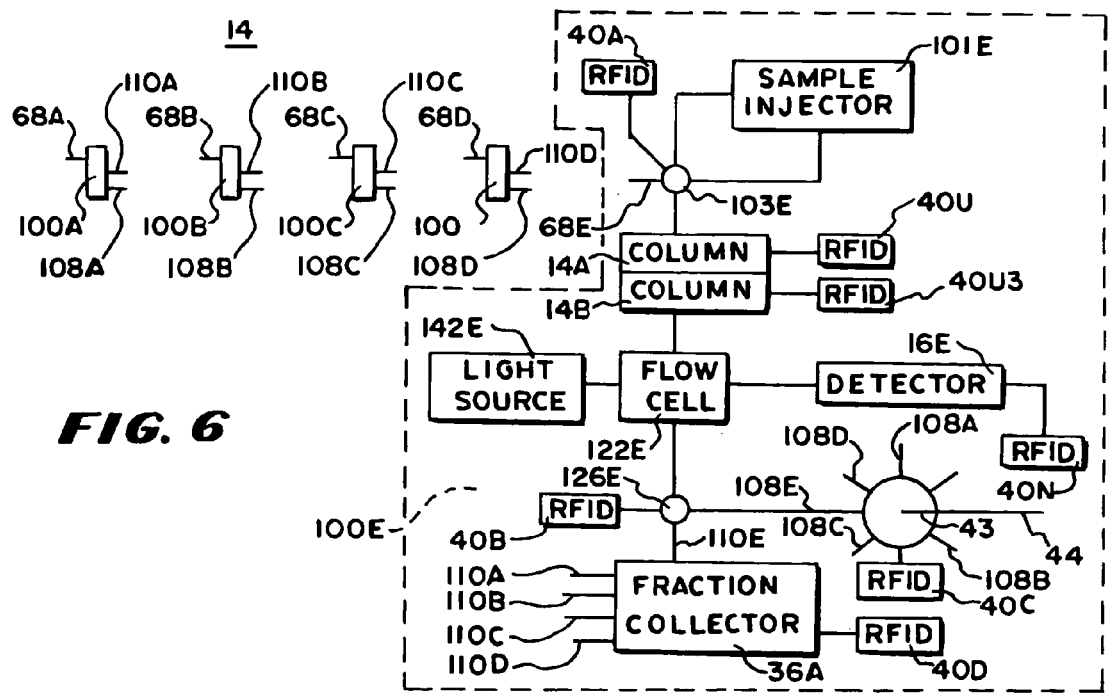
FIG. 6 is schematic diagram of a column and detector array forming part of the embodiment of FIG. 5.

In FIG. 6, there is shown a schematic diagram of a column and detector array 14 having a plurality of columns and detectors, five of which are indicated as 100A-100E, a corresponding plurality of outlet conductors 68A-68E, a corresponding plurality of solute outlets 110A-110E, a corresponding plurality of waste outlets 108A-108E from the manifold 42 (FIG. 4) and a fraction collector 36A (FIG. 4). In the preferred embodiment, there are ten columns and detectors. For illustration, the columns and detectors 100A-100D are shown as a general block whereas the column and detector 100E is shown in greater detail with the understanding that the columns and detectors 100A-100D are substantially the same. Moreover, while five columns and detectors are shown to correspond with the example being used in this application, more or less could readily be used and ten are used in the preferred embodiment.

The column and detector 100E includes an injector system 102E, a column stack 14A and 14B in the column and detector array 14, a detector 16E in the column and detector array 14, a waste outlet 108E and the solute outlet 110E. With this arrangement, solvent, whether a gradient or not, flows in the conduit 68E through an injector 110E, through the column stack 14A and 14B within the column and detector array 14, a flow cell 122E, where solute may be detected and from there into the collector system 16 (FIG. 4) for the collection of solute and the disposal of waste. The column stack (14A and 14B in FIG. 6) may instead be any type of chromatographic column regardless of the mode of operation and it is generally packed in accordance with the separation problem. In the preferred embodiment, the column is REDISEP DISPOSABLE COLUMNS sold by Teledyne Isco, Inc., 4700 Superior Street, Lincoln, Nebr. 68504. It is mounted to either receive a sample injection manually from a syringe or automatically from the injector 101E as well as receiving solvent on the outlet conductor 68E. Its outlet flows through the detector system in the column and detector array 14.

In FIG. 6, the column stacks 14A and 14B are shown for illustration. The outlet of the column 14A communicates with the inlet of the column 14B in a manner known in the art so that the inlet port of the column 14A receives solvent and sample from a valve 103E and the outlet port of the column 14B is delivered to the flow cell 122E. In this arrangement, the wireless communication device 40U is connected to communicate with the column 14A and the wireless communication device 40U3 is connected to communicate with the column 14B. These wireless communication devices each contain information about their characteristics so that a reader and microprocessor may compare the information and determine if the connection is correct or not and convey this information appropriately to the user such as through a display or alarm or inhibiting the operation of the pumps through the controller 18 (FIG. 4). For example, there may be recorded on the wireless communication devices associated with the columns: (1) the past history complete enough to avoid incompatible solvent systems by having the microprocessor with which it communicates indicate the incompatible use; (2) a sample chromatographic curve for use by the chromatographer; (3) a calibration curve; (4) the precision or an indication of the precision of the column construction which may be used to grade the column so that better grade columns may be sold to higher price markets; (5) flow rates; (6) pressures; (7) solvent mixtures; (8) pH; (9) conductivity; and (10) dissolved oxygen and the like. The efficiency of the column with certain chemistries or processes can be determined and recorded.

At the start of the chromatographic run, the wireless communication device 40J (FIG. 3) attached to the sample injector 20 (FIG. 3) receives a signal from the wireless communication device 40U (FIG. 4) that communicates with the controller 18 (FIG. 4) and in turn switches the valve 103E so that solvent flows into the injector 101E and from the injector through the column (14A, 14B) and into the flow cell 122E for detection of bands.

The detection system includes a light source 142E, the flow cell 122E, the detector 16E and a valve 126E for channeling fluid either to the waste outlet 108E through a conduit 44 or to the collector outlet 110E. The light source 142E, hereinafter referred to as the optical bench, applies light from a source common to each of the column and detector assemblies 100A-100E and applies it through each of the corresponding ones of the flow cells including the flow cell 122E and from there to the corresponding detectors including the detector 16E. The signal received indicates the effluent to be channeled to the collector 36A and that to be channeled to the waste 44 (FIG. 4) for the particular column and detector system.

The injector 101E includes a solid sample load cartridge in the preferred embodiment and a four-way manual selective valve 103E for controlling the selection of sample and injection into the columns 14A and 14B. In the embodiment of FIG. 6, an individual injector system (injector system 101E being shown in FIG. 6) is provided for each of the columns although the outlet from one injector could go to a manifold to supply the same sample to a plurality of columns and/or the outlet from one injection cartridge could go to a plurality of injection valves if desired. Similarly, a single fraction collector 36A is shown but a plurality of such collectors could be used with the individual valves connected to more than one collector.

The injector system 101E includes the four-way valve 103E for alternately injecting sample from the sample injector 101E, which in the preferred embodiment is a cartridge, and selecting the solvent gradient from the outlet 68E from the pumping system. Thus a sample may be injected and then by turning the manual valve 103E, the chromatographic run may be initiated. While a manual four-way valve 103E is shown, automatic injector valves are also available and may be utilized.

In FIG. 7, there is shown a block diagram of the chromatographic system 10A having fraction collector diverter valves 214, a flow cell and detector array 124, the controller 18, a pressure transducer 218 and a valve array 212 for pumping solvents. This block diagram illustrates the connections through wireless communication devices between for example the controller 18, a pump drive motor 32A, the fraction collector diverter valves 214, the column and detector array 14 (FIG. 4) and the valve array 212. As shown in FIG. 7, the controller 18 includes inter alia functional components such as a pump controller 200 and a valve and detector controller 201. The valve array 212 includes pump mixing valves 70, inlet valves 72 and purge valves 94.

As shown in FIG. 7, the pump controller 200 is connected to the pump drive motors 32A and the pressure transducer 218 in a feed-back arrangement such as that described in U.S. Pat. No. 5,360,320, the disclosure of which is incorporated herein by reference. Specifically, the feed-back circuit disclosed in connection with FIGS. 8 and 9 in columns 11, 12, 13 and 14 of U.S. Pat. No. 5,360,320 for controlling the pump disclosed in FIG. 6 of that patent is utilized here. The pump controller 200 also interacts with the valve and detector controller 201 to control the flow cell and detector array 124 and the fraction collector diverter valves 214 for the fraction collector 36A (FIG. 6). The valve and detector controller 201 supplies signals to control mixing valves 70A-70J (shown collectively at 70 in FIG. 7), the inlet valves 72A-72J (shown collectively at 72 in FIG. 7) and the purge valves 94 of the valve array 212. With this arrangement, the detection of bands to be collected controls the fraction collector valves to channel the collection into the appropriate containers.

This system operates as described in U.S. Pat. No. 6,427,526 except instead of hard wiring between the units, wireless communication devices transmit data or packets of data to control the operations thereof.

In FIG. 8, there is shown a simplified perspective view of a column 14 having a first wireless communication device 40U1 and a second wireless communication device 40U2 positioned 180 degrees from each other. In FIG. 8, they are shown mid-section of the column but may be positioned anywhere in the column where they will be in reasonably close communication with a wireless receiver. By positioning them 180 degrees apart, the column becomes insensitive to the rotational orientation since one or the other of the wireless communication devices will have an unobstructed communication path to a receiver mounted on the casing of the chromatographic system.

In FIG. 9, there is shown a perspective view of a fraction collector 36 including a main frame 46 and a plurality of racks such as a first test tube rack 50 and a second test tube rack 52 exploded away and turned to show its bottom side. The main frame includes a touch screen or LCD display 48, a distributor arm 60, an RFID reader 56B, a wireless communication device 40K. Each of the test tube racks 50 and 52 has a wireless communication device 40K, which in the preferred embodiment is an RFID device mounted to its bottom side where it may come in proximity to a reader such as the RFID reader 56B. The readers and wireless communication devices determine if a rack is in position and may identify the rack such as by the number of openings and cross sections to provide proper identification for the distributor arm 60 to move into position and distribute fluid into the appropriate tubes such as a test tube 54. In the embodiment of FIG. 9, a fraction collector 36 with two different racks 50 and 52 is shown, one of which is exploded away but each of which may be moved automatically into position where the registration and type may be checked. The information may then be transmitted to the microprocessor associated with the fraction collector 36 to distribute liquids appropriately.

Figure 10:
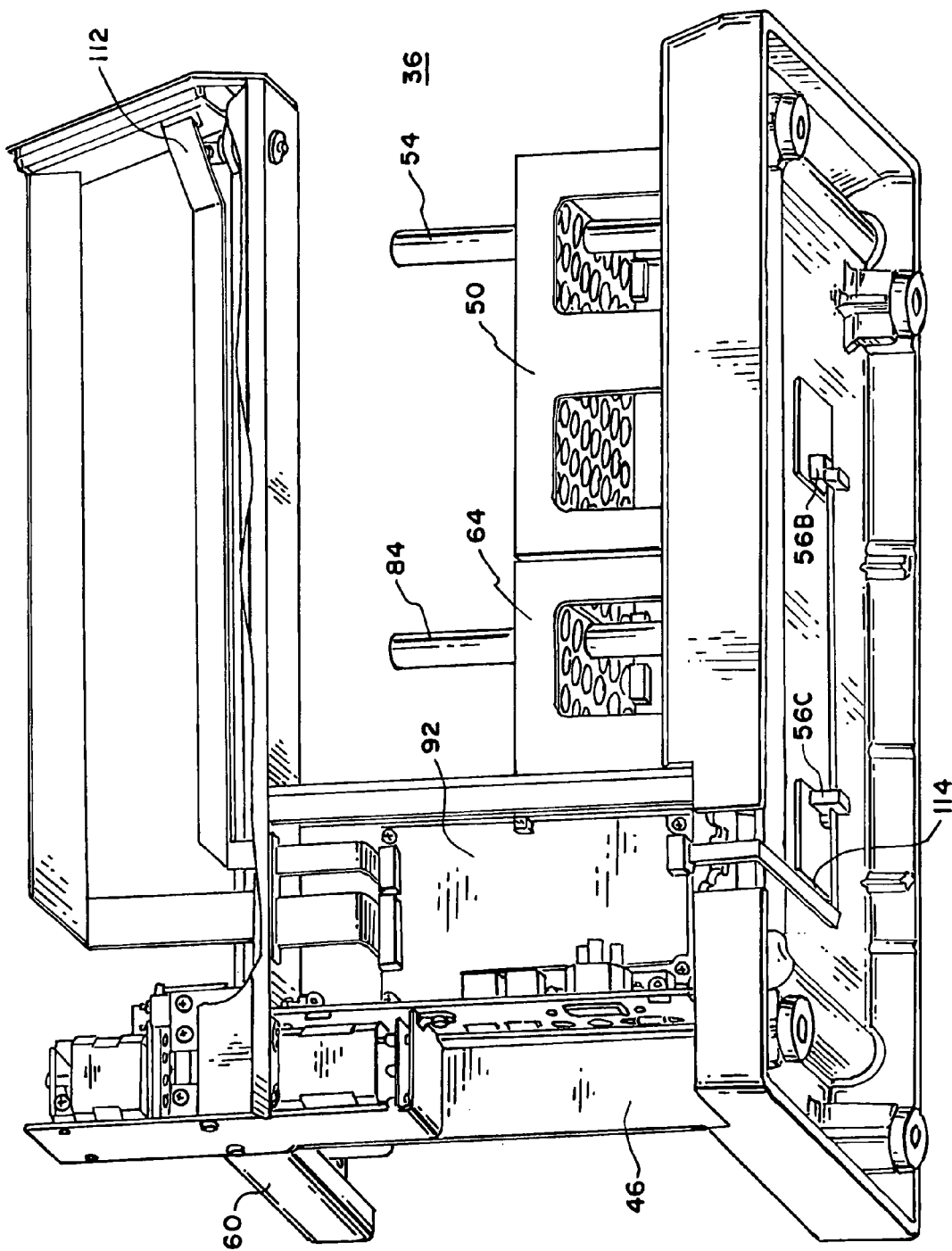
FIG. 10 is a perspective view of the fraction collector of FIG. 9 shown from another angle.

In FIG. 10, there is shown a perspective view of the fraction collector 36 viewed from the bottom and back side showing the distributor arm 60, the main frame 46, RFID readers 56B and 56C connected to an RFID table 114, a conductor ribbon 112 for the LCD display 48 (FIG. 9), and a main circuit board assembly 92. The first test tube rack 50 and a third test tube rack 64 are shown positioned within the fraction collector 36. The first test tube rack 64 is a 96 opening rack or any other appropriate size rack having the tube 84 within it and the test tube rack 50 is a 48 opening rack showing as an example a test tube 54 within it.

In operation, the RFID devices such as 40K (FIG. 3) contain an identification of the test tube rack by the arrangement of tubes in the sizes within it so that when they register with the appropriate RFID reader 56A (FIGS. 3 and 4), 56B and 56C, the reader can indicate to the main circuit board 92 that the test tube rack is in place to control the distributor arm 60 to distribute effluent in the proper tubes or to waste. The RFID readers 56A (FIGS. 3 and 4), 56B or 56C may also contain information about the size of the test tubes 54 and 84 in the test tube racks so that the controller 18 (FIG. 3) may receive this information from the RFID reader 56A (FIGS. 3 and 4) and initiate a program that will move the distributor arm 60 to collect the sample if necessary in successive tubes and avoid overflow. The RFID devices such as the RFID wireless communication device 40K (FIG. 9) in the second test tube rack 52 (FIG. 9) can identify the samples collected in the test tubes, provide the test tube configuration and identify the fractions or the like as well as including user identification so that the test tube rack may continue to supply user information to other processing units as needed and control the distribution of the samples. Moreover, this information may be utilized by transfer devices to transfer the samples for use with other analytical equipment such as spectrometers or the like and may be used with corresponding devices in the spectrometer for further processing and transfer of information such as to electronic notebooks.

The wireless communications system in the preferred embodiment uses RFID tags such as the Q5 programmable RFID tags sold by Sokymat and operating at 125 KHz. The RFID reader modules are ID-Innovations ID-12. They are encoded to identify the two configurations, number of tubes and volume of the tubes.

Although a preferred embodiment of the invention has been described in substantial detail, many modifications and variations of the invention are possible in light of the above description. Accordingly, it is to be understood that, within the scope of the appended claims, the invention may be practiced other than as specifically described.

The invention claimed is:

1. A method of performing liquid chromatography on a sample, comprising the steps of:
   receiving a target time of run resolution input, the target time of run resolution based on a target resolution in a target time;
   determining if a chromatographic column containing shape stabilized packing is present;
   applying sample to the chromatographic column containing shape stabilized packing;
   pumping liquid phase through the chromatographic column containing shape stabilized packing at a rate of flow at least 20% to 50% greater than a standard rate of flow to obtain the target time of run resolution.

2. A method of performing liquid chromatography in accordance with claim 1 wherein the liquid chromatography is flash chromatography.

3. A method in accordance with claim 2 wherein a liquid chromatographic column has an inner diameter greater than 20 mm.

4. A method in accordance with claim 1 wherein at least one of a rate of flow and a gradient slope is selected in accordance with the resolution required.

5. A cost effective liquid chromatographic method, comprising the steps of:
   receiving a target time of run resolution input, the target time of run resolution based on a target resolution in a target time;
   running at least one pilot run on a sample, the pilot run including a run time, a gradient slope, and a flow rate;
   determining if the at least one pilot run met the target time of run resolution;
   shortening a run time, increasing a gradient slope and increasing a flow rate for samples for which the at least one pilot run provides a time of run resolution greater than the target time of run resolution.

6. A method of liquid chromatography, comprising the steps of:
   programming at least one gradient run with at least one gradient profile for a sample;
   determining whether the at least one gradient profile provides a target resolution and a target time of run resolution for the sample;
   performing chromatography on the sample with the at least one gradient run for samples in which the target resolution and target time of run resolution were met with the at least one gradient run and increasing a rate of flow for samples in which the target resolution was exceeded whereby the time of run resolution is decreased.

7. The method of claim 6 in which the step of programming at least one gradient run includes the step of using TLC to determine whether the target resolution and target time of run resolution are met.

8. The method of claim 6 in which the step of programming at least one gradient run includes the step of making a pilot run to determine whether the target resolution and the target time of run resolution are met.

9. The method of claim 6 in which the step of programming at least one gradient run includes the steps of:
   increasing a rate of flow of solvent by at least 10 percent and a gradient slope by at least 10 percent for a first trial run;
   decreasing the rate of flow of solvent and decreasing the gradient slope for pilot runs in which the target resolution is not met and increasing the rate of flow and the gradient slope for pilot runs in which the target resolution is exceeded.

10. The method of liquid chromatography of claim 6 wherein determining whether the at least one gradient profile provides a target resolution and a target time of run resolution for the sample further comprises the steps of:
   measuring a first separation between a first peak and a second peak;
   receiving the target time of run resolution;
   comparing the first separation with the target time of run resolution;
   increasing a flow rate of a solvent to achieve the target time of run resolution if the target resolution has not been met by the first separation;
   measuring a second separation between the first peak and the second peak; and
   increasing a gradient to achieve the target time of run resolution if the target resolution has not been met by the second separation.

11. The method of liquid chromatography of claim 6, wherein determining whether the at least one gradient profile provides a target resolution and a target time of run resolution for the sample further comprises the steps of:
   programming at least one gradient run with at least one gradient profile, the at least one gradient profile including the target time of run resolution; and
   altering the at least one gradient profile by increasing a flow rate of a solvent to improve the separation between a target component and a closest impurity.

12. A method of identifying, separating or purifying a target component using column chromatography, comprising the steps of:

determining resolution with a standard gradient;
identifying a poorly resolved target compound with a high equivalent plate height;
making a chromatographic run with a gradient no greater than the standard gradient but with a flow rate greater than a standard flow rate; and
separating or purifying a well resolved target component, making a chromatographic run at a higher flow rate and a gradient no steeper than the standard gradient.

* * * * *